United States Patent [19]

Green

[11] Patent Number: 4,473,671

[45] Date of Patent: Sep. 25, 1984

[54] FORMABLE ORTHOPEDIC CASTS AND SPLINTS

[75] Inventor: Richard Green, Livingston, N.J.

[73] Assignee: Johnson & Johnson Products, Inc., New Brunswick, N.J.

[21] Appl. No.: 528,695

[22] Filed: Sep. 1, 1983

[51] Int. Cl.³ .................... A61F 13/00; C08K 3/34; C08L 75/04
[52] U.S. Cl. .................................. 523/105; 128/90; 128/156; 523/111; 524/456
[58] Field of Search ............... 128/90, 156; 523/105, 523/111; 524/456

[56] References Cited

U.S. PATENT DOCUMENTS

| | | | |
|---|---|---|---|
| 4,105,025 | 8/1978 | Wang et al. | 128/90 |
| 4,143,655 | 3/1979 | Custer et al. | 128/156 |
| 4,156,067 | 5/1979 | Gould | 128/156 |
| 4,233,969 | 11/1980 | Lock et al. | 128/156 |
| 4,316,457 | 2/1982 | Liegeois | 128/90 |

*Primary Examiner*—Allan Lieberman
*Attorney, Agent, or Firm*—Michael Q. Tatlow

[57] ABSTRACT

A cast material comprising a filled crystalline polyurethane is disclosed. The filler is present in an amount of from 30% to 60% by weight composition. The filler comprises from 20% to 60% by weight of calcium metasilicate fibers and from 40° C. to 85° C. by weight of silica.

7 Claims, No Drawings

FORMABLE ORTHOPEDIC CASTS AND SPLINTS

BACKGROUND OF THE INVENTION

A. Field of Invention

This invention relates to thermoplastic splint and cast forming material in the form of a bandage, web, film, tape or sheet material. Such splints and casts are useful in the treatment of the human and animal body for the maintenance of immobilization, fixation and bracing following reduction of fractures and dislocations and the maintenance of approximation of bone fragments following reduction of fractures. The invention relates to the use of crystalline polyurethane polymers which contain a filler and which may be softened by heat and shaped to conform to the body and which recrystallize upon cooling to form a rigid, self-supporting cast or splint.

B. Description of the Prior Art

Heretofore, cast materials such as plaster of Paris have been extensively used but casts made from such materials are heavy, bulky, sensitive to water and have poor X-ray penetrability. Aluminum splints, lined with soft polyether foam, have also been used but are difficult to properly shape and to fasten to the portion of the body intended to be immobilized.

The use of specific thermoplastic materials in casts and splints is known. U.S. Pat. No. 2,385,879 discloses the use of a copolymer of a vinyl ester of an aliphatic acid and a vinyl halide. U.S. Pat. No. 3,420,231 discloses a fibrous substrate coated with a mixture of trans-1,4-choroprene and an inversely soluble resin such a methyl cellulose. U.S. Pat. No. 3,442,265 discloses the use of polymethyl methacrylate and U.S. Pat. No. 3,809,600 discloses transpolyisoprene. Foamed thermoplastic materials such as polyethylene, U.S. Pat. No. 2,947,307, and foamed polyurethane formed in situ, U.S. Pat. No. 3,301,252, have also been disclosed.

These prior materials and methods for forming splints, braces, supports or casts have met with little practical success because of one or more disadvantages attending their use. In some cases, they are difficult to apply or mold and involve complicated heating and water treatments or other manipulating steps. In other cases, separation of components, such as plasticizers, from the splint, brace, support or cast containing same can cause discomfort and in some instances, extreme irritation to the skin of the patient. In still other cases, the splint, brace, support or cast is water sensitive, lacks sufficient strength or rigidity, is difficult to reliably fasten to the body portion being corrected and/or is difficult to remove when no longer needed. Crystalline polymers, which melt at temperatures of from about 35° to 100° C. can be used as splints, or casts provided such polymer can be molded at a temperature which will not harm the skin. These materials rely on the recrystallization to provide strength to the splint or cast; the amorphous polymer being pliable. Many of these materials can be "worked" at temperatures below the recrystallization temperature for a time so that the splint or cast may be formed at a comfortable temperature and only time is required to obtain strength through recrystallization. However, many of these materials recrystallize at too slow a rate taking for up to thirty minutes while waiting for sufficient recrystallization of the polymer to occur. Of course, the polymer may be artificially cooled, for example, by placing in cold water. This additional step is inconvenient for both the patient and the orthopedist. U.S. Pat. No. 4,105,025 discloses the use of a crystallizable polyurethane polymer applied to a fibrous substrate. The use of this polymer avoids some of the problems that were encountered with the thermoplastic polymers previously mentioned. However, the splint or cast materials, as disclosed in U.S. Pat. No. 4,105,025, do not have adequate hardness or modulus properties. When such casts or splints are applied to a body, the heat of the body softens the materials to the point where they will no longer provide adequate support. In addition, the recrystallization or set time, that is, the time required for the unfilled polymer cast or splint to reharden after it has been softened by heat, is too long to be acceptable. The set time should be ten minutes or less.

It would be expected that the addition of inert fillers could be employed to improve the hardness and modulus properties of the polyurethane polymer casts or splints. It has previously been determined that the simple addition of a filler, e.g., wollastonite or a filler and coupling agent to the polymer will not overcome these deficiencies. If sufficient filler is added to the polymer to give adequate hardness, the cast material becomes excessively brittle on recrystallization. The excessively brittle casts tend to crack and break and become useless as a support for a limb. The excessive brittleness is particularly detrimental when the cast material is used in a body cast or a scoliosis jacket. A scoliosis jacket is often removed and replaced on a patient. If the cast material is brittle, the cast will break when it is removed.

SUMMARY OF THE INVENTION

The present invention overcomes the problems of prior casting materials by using a specific combination of inert fillers with a crystalline polyurethane polymer. The combination of fillers results in a splinting material that has desired strength, rigidity, set time and does not become brittle in use.

This invention, therefore, provides formable orthopedic casts and cast materials in the form of sheets, tapes, films and preformed contour fitting shapes for application to the human or animal body to form a splint, brace, support, protective shield or cast thereon. The orthopedic cast materials of this invention are characterized as having excellent working time while hardening at a rate which is desirable to the orthopedist applying these materials to a patient. The term "cast" as used herein is intended to include splints, supports, braces, shields and other similar orthopedic devices. The casts and cast materials are made with a crystalline polyurethane polymer which is more fully described hereinafter. The invention also provides methods for making such formable, orthopedic cast materials and for making such splints, braces, shields, supports and casts. Furthermore, this invention provides a method of varying the recrystallization rate of crystalline polyurethane polymers.

The cast materials of this invention are very easily and rapidly applied to the human or animal body to form rigid, non-irritating, strong, durable, water-resistant, soil-resistant, close-fitting splints, braces, supports, shields and casts which are very easily removed when no longer needed, without even the slightest injury or irritation to the patient and without serious damage to the cast material which may be sterilized and used again, if desired. There is no danger of skin irritants or other substances exuding from the cast material before or during application to the patient, and the material can be made self-adhering, as desired.

The webs or sheets of crystalline polyurethane polymer can be of any desired thickness ranging from about 1 to 2 mils or less, such as in the cast of tapes or films, up to about 100 mils or more.

The formable cast material of this invention can be used to make custom, contour-fitting splints, braces and orthopedic or surgical supports. The resulting product can be used to form splints on broken or cracked limbs or other body parts; for injuries to tendons, ligaments and the like; for correcting congenital malformations, such as clubfoot, hip-luxations and the like; or, for shielding and protective purposes for protecting teeth and other body parts. The resulting product can be used to stretch skin to minimize scar tissue formation during burn treatment. The product can be formed into units which cover only a portion of a limb or body part or into units that completely encompass the limb or body part. The splints or surgical support can be used on the human body or for veterinary purposes. The use of the formable cast material allows the elimination of things like aluminum splints and allows injured body parts such as finger joints and the like to be supported in bent positions. The term "orthopedic cast," as used herein, encompasses all of the above uses.

More specifically, the formable cast material can be used to make cock-up splints, opponent splints, hand rest splints, full leg splints, cervical collars, heel protectors, writing aids, shin guards, arthric cones, mouth pieces, tooth guards, arch supports, plantar molds, dynamic splints, and the like.

In use, the orthopedic cast material is warmed into a sufficiently high temperature to cause the polymer therein to become soft enough to deform. The temperature is low enough to cause no added discomfort to the patient during application. The orthopedic cast material is molded to conform to the surface shape of the effected portion of the body and then is cooled to room temperature. Upon cooling (crystallizing), the orthopedic cast, which has been made to conform closely to the effected portion of the body to which it is applied, rigidifies. If desired, the orthopedic cast material can be heated before or after it is placed around or on the effected portion of the body.

The orthopedic cast is easily removed by warming it to a temperature at which it becomes soft enough to deform and then the heated orthopedic cast is manually deformed to permit removal from the body. The material can also be removed with the use of cast saws or shears.

The casts made from the flexible cast material are rigid; easily and rapidly molded during application; strong; durable; not sensitive to water, stain resistant; close fitting to the surface of the body; not irritating to the skin; easily removed by heating (e.g., with hot air or water or cutting); X-ray; translucent; customized; non-toxic and non-allergic; can be used over and over; can be washed with any detergent; is a non-conductor of heat; is easily cut with scissors or a knife when warm or cold, leaving a smooth edge. Because the cast can be custom made from sheets, films and the like, a number of sizes or designs or casts need not be stocked. Persons wearing the casts or this invention can swim and engage in other activities without damage to the cast.

Another property of the filled crystalline polyurethane polymer base of the instant invention is its compatibility with a wide range of diverse materials thus permitting the blending of a medication into the cast material when it is formed.

DETAILED DESCRIPTION OF THE INVENTION

The crystalline polyurethane is a thermoplastic material having a melting point or softening temperature of from 35° C. to 240° C., preferably from 45° C. to 85° C. These polymers may be the reaction product of a polyfunctional isocyanate and an organic compound having more than one active hydrogen, e.g., a polyfunctional polyester, polyether alcohol, or amine or any combination thereof hereinafter referred to as the isocyanate reactant. In general, essentially linear polymers are preferred, therefore, a difunctional isocyanate is reacted with an organic compound having two active hydrogens, e.g., a polyester or polyether and chain extended with a glycol or amine. Preferably, a difunctional polyester chain extended with a glycol is utilized as said polyurethane.

The difunctional isocyanate may be monomeric or polymeric in nature. Examples of suitable difunctional isocyanates include: 1-Chloro-2,4-phenylene diisocyanate, m-Phenylene diisocyanate, p-Phenylene diisocyanate, 4,4″ Methylenebis (phenyl isocyanate), 2,4-Tolylene diisocyanate, Tolylene diisocyanate (60%, 2,4-isomer, 40% 2,6-isomer), 2,6-Tolylene diisocyanate, 3,3′-Dimethyl-4,4′-biphenylene diisocyanate, 4-4′-Methylenebis (2-methylphenyl isocyanate), 3,3′-Dimethoxy-4,4′-biphenylene diisocyanate, 2,2′,5,5′-Tetramethyl-4,4′-biphenylene diisocyanate and 80% 2,4-, and 20% 2,6-isomer of tolylene diisocyanate with diethylene glycol adipate polyester.

Polyesters are preferred as the isocyanate reactant, especially those having a sufficiently high molecular weight so as to impart the required crystallinity to the polyurethane polymer. For example, hydroxyl terminated polyesters such as poly-caprolactone or those based on adipic acid are especially preferred. These polyesters may have a molecular weight of from 500 to 5,000 preferably from 2,000 to 4,000.

The isocyanate and the isocyanate reactant may be reacted to form crystalline, polyurethane polymers by methods known in the art. For example, see Polyurethanes, Dombrow, Reinhold Publishing Corp. N.Y. 1957.

The crystalline polyurethane polymers will have a high degree of crystallinity contributed by the polyester component and preferably will have a number average molecular weight of from 25,000 to 100,000.

In order to have the desired properties in the finished cast, it is necessary that the polyurethane polymer contain a filler. The filler must be present in an amount of from 30 to 60% based on the total weight of material.

The addition of filler to the crystalline polyurethane is necessary to give the desired hardness, rigidity and modulus properties to the cast. Without filler, the polyurethane cast will tend to be softened by the body heat of the patient wearing the cast. As the cast softens, it loses its rigidity and no longer serves its intended purpose.

The filler used in making the cast material of the present invention is a combination of two commercially available fillers, wollastonite and novacite. Wollastonite is a naturally-occuring, nonmetallic calcium metasilicate, $CaSiO_3$. Its form is acicular, i.e., needlelike, with typical length to diameter ratios ranging from 3:1 to 20:1. Novacite is 99.5% Silica, $SiO_2$, in the form of microcrystalline platey particles 1 to 10 microns in diameter. The filler of the present invention contains from 20% to 60% by weight (based on the total weight of filler) of wollastonite and 40% to 80% by weight of novacite. Increasing the percentage of wollastonite tends to form a cast material that is too brittle, and decreasing the percentage of wollastonite results in a cast material that does not have the desired strength and rigidity. The preferred combination of fillers contains 50% wollastonite and 50% novacite.

The total amount of combined filler present in the cast material is from 30% to 60%, with 50% of filler being preferred. Filler loadings below 30% result in inadequate rigidity and set time of the cast material, and filler loadings above 60% are very difficult to incorporate into the polymer, and the cast material becomes brittle.

The crystallinity of the polyurethane can be increased by the addition of a coupling agent to the filler. The coupling agents that have been found to be particularly useful are titanates of the formula:

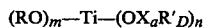

wherein R is a hydrocarbyl radical or a hydrocarbyl radical substituted with inert substitutions such as halogens, oxygen, sulfur, and phosphorous, preferably R is $C_1$ to $C_{10}$ hydrocarbyl radical especially alkyl or alkenyl radicals, and most preferably R is a $C_1$ to $C_4$ alkyl radical such as methyl or isopropylradical; X is a divalent phosphato, pyrophosphato, or sulfyl radical, preferably a phosphato or pyrophosphato radical; R1 is a hydrocarbyl radical or a hydrocarbyl radical substituted with the above inert substituents e.g., a $C_1$ to $C_{100}$ alkylene radical; and a, b, m and n are integers with $1 < m < 4$, $m+n=6$, and a and b are 0 or 1. Preferably m is 1 and n is therefore 5. It should also be noted (as exemplified below) that R, R1 and X can represent different radicals in the same titanate coupling agent. The above coupling agents may terminate at the end of the R or $R^1$ groups with a reactive radical such as an acrylate, methacrylate or vinyl radical. It is not believed such terminal reactivity is important for the coupling agent to function as a recrystallization increasing agent within the scope of the instant invention.

Specific examples of the above include isopropyl triisostearoyl titanate, isopropyl tri(lauryl-myristyl) titanate, isopropyl isostearoyl, dimethacryl titanate, isopropyl tri(dodecyl-benzenesulfonyl) titanate, isopropyl isostearoyl diacryl titanate, isopropyl tri(diisooctyl phosphato) titanate, isopropyl trimethyacryl titanate, isopropyl tri(dioctyl-pyrophosphato) titanate, and isopropyl triacroyl titanate.

The preferred titanate is isopropyl tri(dioctyl pyrophosphato) titanate:

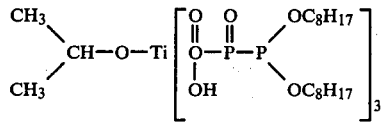

The coupling agent may be present in an amount of from 0.05 to 5, preferably 0.25 to 1 weight percent of said crystalline polyurethane polymer and filler.

It is also possible to employ small amounts, i.e., 10% or less, of other filling materials such as titanium dioxide to whiten the cast materials.

Any suitable method of preparing the formable cast materials can be used. For example, the crystalline polyurethane polymer can be fluxed on a two-roll mill or in a suitable mixer by heating to moderate temperatures, e.g., about 60° C. or more and the filler and/or the recrystallization increasing agent added to the fluxing polymer. Then, the crystalline polyurethane polymer or blend is sheeted, extruded in the form of tape or film or extruded and pelletized and compression molded into plaques, sheets, or other desired shapes, or otherwise shaped or formed into any desired configuration.

The preferred method of forming the cast material is by milling or calendering. It is advantageous to include a microcrystalline wax as a processing aid when preparing the cast material by milling or calendering. Typically approximately ½% to 3% by weight of the wax (based on the total weight of the formulation) is included.

In addition, powders or granules of the crystalline polyurethane polymer or blend can be dissolved or dispersed in solvent, cast on a hard impermeable casting surface to form a sheet or film or spread on the flexible base or substrate and dried. Suitable solvents include tetrahydrofuran, N,N-dimethyl formamide, methyl ethyl ketone and other solvents. Fast drying solvents are preferred when the crystalline polyurethane polymer is applied as a solution to a casting surface or flexible base.

Another method of bonding the crystalline polyurethane polymer or blend to the base web or sheet is to dust the base web or sheet with powdered or granulated polymer followed by warming to temperatures at which the polymer melts and coalesce on or in the surface of the base web to form a coating or impregnation.

The cast material can be perforated to permit diffusion of air or moisture from and to the skin covered by the cast material after it is applied to the human or animal body. The size of such perforations is not narrowly critical and can range from about 1 mil to about ¾ in. in diameter. In a cast made from such formable cast material the series of holes or perforations promote evaporation of the perspiration moisture produced underneath the cast when it is in use on the human or animal body and which further reduces the weight of the already light cast.

The web or sheet of flexible cast materials should have a thickness between about 1/16 inch and about ¼ inch. Thicker sheets may be more difficult to bend in the many cases and thinner sheets may be too weak unless overlapped and may cool too quickly to fuse easily unless heat is applied after formation of the cast on the body portion. The exact thickness depends also upon the location of the body where the cast is to be applied. A thickness of 1/16 inch may be preferred for finger and toe casts, and a thickness of ¼ inch may be preferred for larger limbs. Where greater strength and rigidity is desired, webs or sheets thicker than ¼ inch can be used.

Also, for example, considerably greater thickness is desirable when the cast material is used in the formation of such devices as arch supports. Where great strength and rigidity is not of paramount importance and where overlapping is convenient webs or sheets considerably thinner than 1/16 inch can be used. The length and width of the cast material will vary according to its type and application, for example, a 10"×10" sheet or 8"×2' sheet has been found satisfactory for arm applications and a 10"×30" sheet has been found satisfactory for leg applications. To form many casts, e.g., those for fingers, toes, arms, legs, and the like, the cast material can be preformed into a tubular shape or other preformed shape. In other instances, the cast material in sheet form is molded around the body area and, if desired, is overlapped, is fused to itself by elevated temperature, and is held in place until it sets by cooling. The cast material can be heated by means of an ordinary home hair dryer, a specially designed heat gun or simply by immersing it in a pan of hot water drawn from an ordinary hot water tap. The cast material can also be used in the form of a tape or elongate sheet by successively wrapping it around the body part in an overlapping manner. Heat applied before or after wrapping causes the overlapping tape to bond together into a unitary cast which sets upon cooling.

The casting materials of the present type should have sufficient strength to support the limb or portion of the body which is intended to be immobilized. The strength is measured and expressed as the bending modulus of the material. The bending modulus is the force necessary to break a sample of rigid material by bending the material until it breaks. The test method to determine bending modulus is ASTM D-790. For general purpose casting materials, i.e., finger, arm or leg casts or splints, the bending modulus should be at least 50,000 pounds per square inch. For full body casts or scoliosis jackets, the bending modulus must be considerably higher, in the range of 100,000 to 120,000 pounds per square inch.

In addition to the strength requirement of the cast material, the cast material should not be brittle. The cast material should be capable of flexing without cracking or breaking. The flexibility of the cast material is determined by bending a sample of the material until the sample breaks. The material should be capable of bending 10,000 times before breaking to be an acceptable cast material.

The orthopedic cast material can be oriented by stretching it while it is warmed to a temperature below its melting point and cooling it while it is in its stretched condition. When in tubular shape, the oriented material can be placed on a limb and heated whereupon the material shrinks into place about the limb. Of course, care must be taken that the tubular material is large enough and/or the extent of shrinkage is so controlled that circulation is not cut off. The oriented material, in tube, sheet or strip form, also can be placed over and shrunk on a previously hardened cast to give a neater, smoother surface, if desired.

The heat needed to raise the temperature of the crystalline polyurethane polymer in the cast material to render it deformable into a cast can be applied in any manner. The preferred manner is to use a thermostatically controlled heat gun, water bath or over although in some cases an ordinary heated-air hair dryer can be used. The cast can be first heated and then put on, or first put on and then heated and held in place while it cools and sets.

The products of the instant invention are formulated to be flexible, after heating, at temperatures which are comfortable to the human body and the remain flexible at these temperatures for a sufficient time so that a cast may be formed to immobilize the fractured limb or brace the injured body may be molded or shaped on the body.

Therefore, the cast material can conveniently be heated to temperatures as low as 50° C. to 85° C. and when flexibilized, the cast material is manually molded into the desired shape and cooled to set its shape. Of course if a flexible base is used, it should be chosen so that the flexible cast material can be melted without decomposing or damaging the flexible base. Of course, the most important consideration is the use of a flexible cast material that can be molded at a temperature which will not hurt or be uncomfortable to the skin. Also, the webs (sheets or strips) can be warmed to near the melting point for patient comfort before being applied, and the material retains enough ductility and formability to form a cast. The material normally sets in about 20 minutes or less when air cooled but will set within 5 minutes or less when compounded with a filler and a recrystallization rate increasing agent.

The following examples are presented wherein, unless otherwise specified, all percentages and parts are by weight and all temperatures are on the Centigrade scale.

EXAMPLE I

A series of cast formulations were prepared with varying percentages of total filler with a polyurethane resin of the following composition. The polyurethane resin is a 1:1 molar reaction product polyhexamethylene glycol adipate (average molecular weight 1,000–3,000); and methylene bis(4-phenylisocyanate). The unfilled polyurethane resin has a crystalline melting point of 51°–55° C. and a number average molecular weight of 79,000. The polyurethane is a commercially available resin Q-Thane PA-29. The filler consisting of equal weight of wollastonite and novacite. For each filler loading, a sample was prepared with a titanate coupling agent ("A" samples in Table I) and without the titanate coupling agent. The set time, or the time for the cast to reharden, is determined by measuring the Shore a Durometer hardness of the cast material after heating in water at 80° C. The cast is set when the Shore Durometer hardness reaches a value of 80. The modulus of the material was determined by the procedure set forth in ASTM D790 at 23° C. The results are shown in Table I. The failure of the samples containing more than 50% filler was brittle failure rather than ductile failure. The samples containing more than 60% total filler are considered to be too brittle to be usable as a cast material. The samples containing less than 30% total filler have set times of ten minutes or more, which is not acceptable.

TABLE I

| Filler | | Set Time Minutes | Modulus × 10³ psi |
|---|---|---|---|
| 0 | 1 | 11 | 27.1 |
|   | 1A | 10 | 22.3 |
| 10 | 2 | 14 | 35.4 |
|    | 2A | 14 | 40.7 |
| 20 | 3 | 10 | 39.0 |
|    | 3A | 10 | 39.9 |
| 30 | 4 | 7.5 | 33.2 |
|    | 4A | 7.5 | 52.9 |
| 40 | 5 | 6 | 78.7 |
|    | 5A | 6 | 71.1 |
| 50 | 6 | 5 | 129.3 |
|    | 6A | 5 | 115.6 |
| 60 | 7 | 4 | 172.3 |
|    | 7A | 4 | 185.9 |
| 70 | 8 | 3.5 | 266.5 |
|    | 8A | 3.5 | 239.0 |

TABLE I-continued

| Filler | Set Time Minutes | Modulus × 10³ psi |
|---|---|---|
| 80 | 9 | Could not mix — |

EXAMPLE II

Another series of formulations were prepared each containing 50% total fillers. The filler contained from 0% to 100% novacite in the filler, the remaining filler being wollastonite. The resin was the same as in Example I. The samples were tested for bending modulus and the number of flexes to failure. The results are shown in Table II.

The flexing test is performed by placing one end of a 1"×3" sample of the material material in a clamp in a horizontial position and bending the free end of the sample approximately ½" up and down at 60 cycles per minute until the sample breaks. Although sample 10, 90% Novacite, withstood more than 10,000 flexes, the bending modulus failure was a brittle failure and this sample was considered to be unacceptable for this reason.

TABLE II

| Sample | % Novacite | Bending Modulus | # Flexes to Failure |
|---|---|---|---|
| 1 | 0 | 109,000 | 4,500 |
| 2 | 10 | 141,000 | 4,500 |
| 3 | 20 | 111,000 | 5,000 |
| 4 | 30 | 127,000 | 1,350 |
| 5 | 40 | 130,000 | 10,000 |
| 6 | 50 | 140,000 | 10,000 |
| 7 | 60 | 130,000 | 11,000 |
| 8 | 70 | 124,000 | 10,000 |
| 9 | 80 | 123,000 | 14,000 |
| 10 | 90 | 112,000 | 12,500 |
| 11 | 100 | 116,000 | 8,500 |

I claim:

1. A thermoplastic casting material having a softening temperature of from 45° C. to 85° C. and capable of recrystallizing to form a rigid self supporting cast within 10 minutes of being softened comprising from 40% to 70% by weight of a crystalline polyurethane polymer and 30% to 60% of a filler, said filler comprising from 20% to 60% of wollastonite calcium metasilicate fibers having a length-to-diameter ratio of from 3:1 to 20:1 and from 40% to 80% of novacite silica in the form of platy particles having a diameter of from 1 to 10 microns.

2. The cast material of claim 1 in which the polyurethane resin has a number average molecular weight between 25,000 and 100,000.

3. The cast material of claim 1 in which the filler contains 0.25% to 1% by weight of isopropyl tri(dioctyl pyrophosphato) titanate.

4. The cast material of claim 1 in which the total filler is present in an amount of 50% by weight of the composition.

5. The cast material of claim 1 in which the filler consists of 50% by weight of wollastonite calcium metasilicate fibers and 50% by weight of novacite silica.

6. The casting material of claim 1 in which the polyurethane resin is the reaction product of polyhexamethylene glycol adipate having an average molecular weight of from 1,000 to 3,000 and methylene bis(4-phenylisocyanate).

7. The cast material of claim 6 in which the total filler is present in the composition in an amount of 50% by weight of the composition, and the filler comprises 50% by weight of wollastonite calcium metasilicate fibers and 50% by weight of novacite silica.

* * * * *